Oct. 15, 1957 R. C. CREELMAN Re. 24,377

SURGICAL OPERATING TABLE FOR SMALL INFANTS

Original Filed Dec. 14, 1953

INVENTOR.
RAYMOND C. CREELMAN
BY
Reynolds, Beach & Christensen
ATTORNEYS

United States Patent Office

Re. 24,377
Reissued Oct. 15, 1957

24,377

SURGICAL OPERATING TABLE FOR SMALL INFANTS

Raymond C. Creelman, Bremerton, Wash.

Original No. 2,751,268, dated June 19, 1956, Serial No. 397,979, December 14, 1953. Application for reissue October 22, 1956, Serial No. 617,674

6 Claims. (Cl. 311—5)

Matter enclosed in heavy brackets [ ] appears in the original patent but forms no part of this reissue specification; matter printed in italics indicates the additions made by reissue.

This invention relates to a novel apparatus by which small infants may be physically restrained and immobilized sufficiently to perform medical examinations and surgery upon them. The invention is herein illustratively described by reference to its presently preferred form; however, it will be understood that certain changes and modifications herein may be made without departing from the essential features involved.

A general object is to provide a convenient and practical device for holding small infants immobilized in the dorsal recumbent position, and to accomplish such result while affording reasonable comfort to the child.

More specific objects include an infant immobilizing device into and from which an infant may be easily and quickly placed or taken, such a device which may be manufactured at relatively low cost, and one which may be easily cleaned and sterilized when necessary. Still another object is an infant immobilizing device which is quite compact and readily portable.

A related object is an infant immobilizing device particularly suited to the performance of circumcision and other operations upon small infants for which general anesthesia is not necessary or advisable.

With these and other objects in view, the novel infant immobilizing device in its preferred form as herein disclosed comprises a generally horizontally disposable infant supporting platform having a cup-like depression or receptacle therein conformed approximately to the dorsal side of the infant's body, said depression including portions respectively providing underlying and lateral support for at least the torso, the legs and the arms of an infant, and preferably also the head. In addition thereto releasable hold-down means are provided in fixed relationship to the platform and are arranged thereon for releasably engaging frontal areas of selected members of the infant's body so as to press and hold the same in the retaining mold. It is found that with comparatively few and localized hold-down elements applied to the infant already partially restrained by the all-embracing mold itself, substantially complete immobility is achieved.

An additional feature of the illustrated device comprises the formation of an elevated instrument supporting table situated between the divergently arranged leg-receiving portions of the platform depression or receptacle.

These and other features, objects and advantages of the invention including certain details of the preferred form thereof will become more fully evident from the following description by reference to the accompanying drawings.

Figure 1:
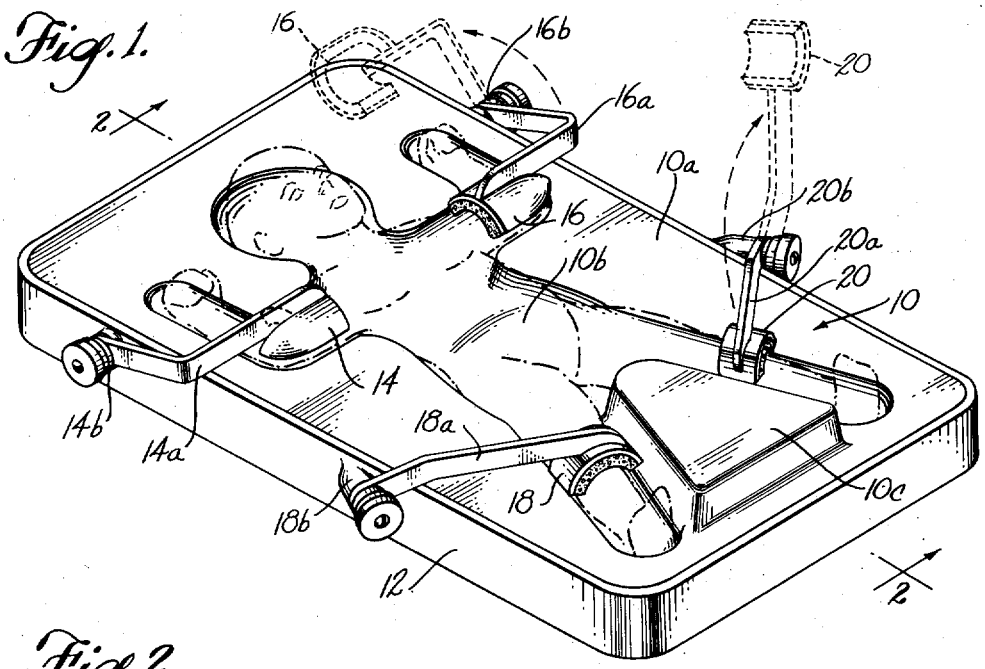
Figure 1 is a perspective view of the preferred form of the infant immobilizing device employing clamp arms as the hold-down means.
Figure 2:
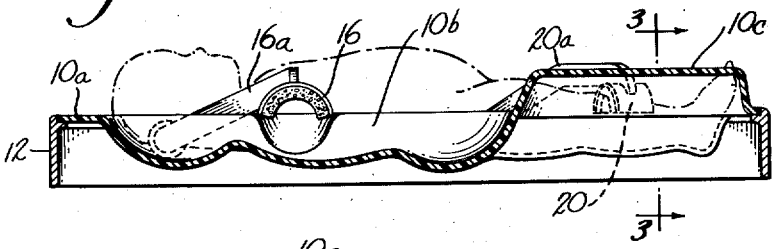
Figure 2 is a longitudinal section taken on the line 2—2 in Figure 1.
Figure 3:
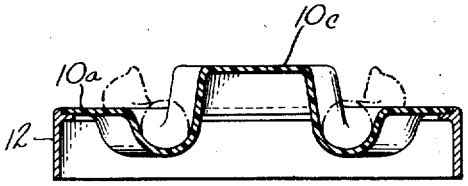
Figure 3 is a transverse section taken on the line 3—3 in Figure 2.

As illustrated, the platform 10 is of generally rectangular proportions, having a substantially flat top surface area 10a extending around the infant receiving receptacle or depression 10b formed therein, except for the elevated instrument table 10c formed between the divergent leg portions of the depression. For reasons of convenience in manufacture, strength, rigidity and ease of cleaning and sterilizing the device it is greatly preferred that the depression 10b of the platform 10 be of a hard, solid and rigid substance rather than of a fabric or like flexible material of similar shape and contour suspended by its marginal edge from a rigid frame formed in the outline of the depression. For similar reasons it is to be preferred that the remainder of the platform, including the marginal portion 10a and the elevated table portion 10c be formed of a similar substance. With such considerations in view it is most practical to manufacture the entire platform structure of a unitary solid construction such as by molding it from a sheet of suitable light-weight plastic material, metal or other suitable substance.

The size, shape and depth of the depression 10b are subject to variation. If the device is to be used primarily in conjunction with the performance of circumcision operations, a single device can be made which will satisfy the vast majority of cases. This is true since operations of this type are usually performed in the first two weeks of life but not until the infant's weight has increased to about seven pounds. It is found, therefore, that a retaining depression 10b cupped approximately to fit an average eight-pound infant will do well for the majority of cases. While fairly close conformity of the depression walls to the body contour is desirable to minimize freedom of movement of the child, nevertheless a small amount of clearance from the infant's body along the depression walls is not objectionable in that regard and is actually preferred to an excessively tight fit creating discomfiture for lack of air circulation around the skin. The walls of the depression should extend well up around the sides of the body members to furnish lateral restraint against physical movement, but should otherwise leave the body exposed as much as possible for access by the surgeon. A depth of depression approximately half the average body thickness is sufficient for most purposes and not excessive. The instrument table 10c, received in the space between the divergent leg portions of the depression, is located at a convenient height in relation to the patient's body and for the purpose mentioned will be situated approximately level with the top side of the immobilized infant.

Preferably the arm portions of the depression are formed so that the infant's upper arms will extend generally oppositely from each other and its forearms will be arranged approximately at right angles thereto.

A base frame 12 of metal extends around the marginal edge of the plastic platform 10 and constitutes a supporting flange thereon by which the device may be rested stably on a horizontal surface. For this purpose the width vertically of this frame exceeds the molded depth of the platform 10 so that the base of the platform depression does not contact any such supporting surface and cause instability. If desired, the platform 10 and supporting frame 12 may both be molded or otherwise formed unitarily of the same material. In Figures 1 to 4 the platform 10 is assumed to be of a plastic substance as mentioned, while the frame 12 is of a suitable lightweight metal such as an aluminum alloy. The platform is retained in the frame with the top surface of the platform substantially flush with the upper edge of the frame.

The hold-down means employed in the illustrated device (Figures 1 to 4, inclusive) comprises two pairs of arm-supported padded contact elements adapted respectively for pressing down against the elbows and knees of the infant and thereby holding both portions of each arm and both portions of each leg against movement out of the receiving depression. Thus the padded contacts 14 and 16 are downwardly cupped to fit over and partly around the bent right and left elbows of the child, respectively, while the generally similar contacts 18 and 20 likewise are formed to fit over and partly around the right and left knees, respectively. For most purposes these four elements of contact with the infant's body, if held firmly against the limbs of the body, are sufficient in conjunction with the highly effective lateral restraint of the conforming mold walls themselves to render the child substantially and completely immobile. If desired, it is readily possible, of course, to provide a torso hold-down means, but such is ordinarily not necessary and in certain instances might constitute a hindrance to the surgeon's activities. Relatively thick, soft and resiliently yieldable pads of sponge rubber or the like are carried by the lower faces of the limb-contoured contact elements so as to afford a good frictional restraining grip on the infant's limbs, minimizing the possibility of rotational and bodily shifting of any limb. Another purpose of such padding is, of course, to avoid hurting the patient while providing a steady, firm pressure downward against the limbs when the contact elements are locked in fixed position.

The arm contact elements 14 and 16 are carried by arms 14a and 16a, respectively, which are pivotally mounted on opposite sides of the base frame 12 to permit raising and lowering such contact elements when necessary. Pivotal supports 14b and 16b for these L-shaped arms provide transversely extending pivot axes such that the contact elements are constrained to swing in parallel vertical planes extending longitudinally of the device. These pivotal supports are located between the head end of the frame and the upper-arm depressions in the platform, so that the arms in their operative positions extend from the respective pivots toward the foot of the device close alongside the frame sides and then turn inwardly toward each other close along the top of the platform. In their inoperative positions, when removed from the patient, the contact elements 14 and 16 will rest against the top side of the platform (see dotted line showing in Figure 1).

The two arms 18a and 20a carrying the respective knee contacts 18 and 20 are also conveniently mounted on opposite sides of the frame 12 by pivotal supports 18b and 20b. These pivots are located generally opposite the patient's crotch, and their axes, contained approximately in the plane of platform 10, are inclined to form rearwardly divergent acute angles with the frame sides. The arms 18a and 20a thus swing in vertical planes which are equally oblique to the longitudinal midplane of the device.

Swinging of the four hold-down arms upwardly into their retracted positions provides free access to the infant receptacle for convenient insertion and removal of a child.

Each of the four arm mounts incorporates ratchet means for locking or holding the respective arms automatically in any of successive closely spaced operative positions. The details of a suitable ratchet mechanism for this purpose appear in Figure 4. The end of the arm 14a, for instance, is keyed on the pivot shaft 20 journaled in the frame side and the retainer cap 22 threaded on the tubular boss 12a projecting outwardly from the frame. The arm swings on shaft 20 in a circumferential slot 12b cut in the side of the boss 12a and is confined by the slot sides against movement endwise of the boss. However, the shaft is free to slide lengthwise through the arm and in the journal apertures which support the shaft. The shaft 20 carries a collar 24 rotatably mounted thereon and having ratchet teeth or radial serrations on one end face positioned to engage complementally formed teeth on the adjacent side of the arm. A longitudinal slot 12c in the inner wall of the boss is engaged by a key 24a on the collar to prevent rotation of the collar while permitting it to move lengthwise therein. An annular groove 20a in the shaft is engaged by a pin 24b through the collar to constrain the two to move lengthwise together while permitting the shaft to rotate separately. A spring 26 encircling the shaft between the cap 22 and collar 24 urges the latter into contact with the toothed side of the arm. The cooperating sets of teeth are so formed that under these conditions the arm may not be lifted, although it may be advanced toward the patient to press the associated contact element carried thereby downward into firm contact with the patient's body. Retraction of the release knob 28 by outward pull thereon compresses the spring and retracts the collar teeth out of engagement with the arm teeth in order to release the arm for upward swinging movement and thereby disengage the associated contact element from the patient. Other types of releasable locking devices for the individual arms may obviously be substituted for the ratchet mechanism shown. It is preferred, however, that each such arm be provided with releasable holding mechanism operated independently of the other arms. If desired, spring pressure may be applied directly to the arms in order to hold their contact elements by spring force against the child.

Figure 5:
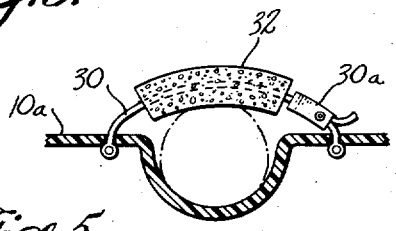
Figure 5 is an enlarged sectional detail of an alternative type of hold-down means usable in the immobilizing device.
Figure 4:
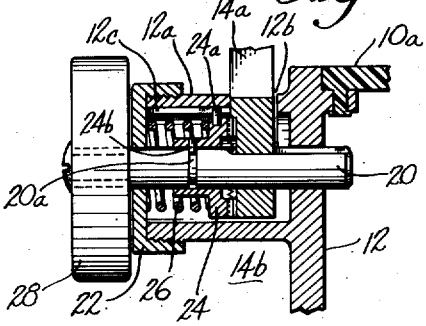
Figure 4 is an enlarged sectional detail of a spring-controlled releasable ratchet means for locking the hold-down arms of the immobilizing device in operative position.

In Figure 5 an alternative hold-down device is illustrated comprising a flexible strap 30 with buckle 30a. The sponge rubber pad secured to the strap serves the same purpose as the contact pads in the preceding form. These and other variations of the novel device will be evident to those skilled in the art.

I claim as my invention:

1. The infant immobilizing device for surgical use and the like, comprising a generally horizontally disposable infant supporting platform of substantially rigid continuous solid sheet form having a depression therein conformed approximately to the dorsal side of a small infant's body, said depression including conjoining portions respectively formed to provide underlying and close lateral support separately for at least the torso, legs and arms of the infant placed in dorsal recumbent position therein, said platform having a generally flat and horizontally disposed marginal portion substantially surrounding the peripheral edge of the depression, and an instrument table portion elevated above said marginal portion located directly between and above the two leg portions of said depression, said leg portions being divergent to provide space therebetween for said table portion, and releasable holder means fixed to said platform and arranged for engagement with frontal areas of selected portions of the infant's body to restrain such body portions against being raised out of said depression, the sides of said depression in the various portions of such depression extending materially upward along the respectively adjacent sides of the corresponding portions of the infant's body and thereby limiting lateral movement of the infant.

2. A surgical operating table for supporting and immobilizing small infants during performance of circumcision and other surgical operations on such infants, said operating table comprising a generally flat table portion formed of solid material substantially impervious to human body liquids and the like, and having a substantially rigid and unyielding surface configuration comprising a cavity shaped in substantial conformity with the dorsal side of the body of a small infant, and including a trunk cavity portion and separate limb cavity portions conjoined with said trunk cavity portion to receive, support and laterally restrain the torso and corresponding limbs of the infant's body placed in dorsal recumbent position therein, respectively, said limb cavity portions comprising generally laterally extended arm cavity portions and divergently extended leg cavity portions, base means constructed and arranged for supporting said table portion in generally horizontal position to receive and support an infant in said cavity, and releasable hold-down means formed and arranged on said operating table to engage the front side of the infant's body at selected locations thereon for rigidly holding the same down in said cavity and thereby against movements interfering with performance of a surgical operation, said hold-down means comprising rigid hold-down members pivotally mounted on the operating table to swing between raised position uncovering the table portion cavity and lowered position in which said hold-down means engages and presses downwardly into said cavity at least the limbs of an infant received in said cavity.

3. A surgical operating table for supporting and immobilizing small infants during performance of circumcision and other surgical operations on such infants, said operating table comprising an infant-supporting platform of substantially rigid form comprising a cavity shaped in substantial conformity with the dorsal side of the body of a small infant and including a trunk cavity portion, arm cavity portions and divergently extending leg cavity portions conjoined with said trunk cavity portion to receive, support and laterally restrain the torso and corresponding limbs of the infant's body placed in dorsal recumbent position therein, base means constructed and arranged for supporting said table portion in generally horizontal position to receive and support an infant in said cavity, and releasable hold-down means formed and arranged on said operating table to engage the front side of the infant's body at selected locations thereon for rigidly holding the same down in said cavity and thereby against movements interfering with performance of a surgical operation, said hold-down means comprising substantially rigid hold-down members movably mounted on the operating table to be shifted between raised position uncovering the infant-receiving cavity and lowered position in which said hold-down means engages and presses downwardly into said cavity at least the limbs of an infant received in said cavity.

4. The infant immobilizing device for surgical use and the like, comprising a generally horizontally disposable infant supporting platform of substantially rigid continuous solid sheet form having a depression therein conformed approximately to the dorsal side of a small infant's body, said depression including conjoining portions respectively formed to provide underlying and close lateral support separately for at least the torso, legs and arms of the infant placed in dorsal recumbent position therein, said platform having a generally horizontally disposed marginal portion substantially surrounding the peripheral edge of the depression, and an instrument table portion located directly between the two leg portions of said depression, said leg portions being divergent to provide space therebetween for said table portion, and releasable holder means fixed to said platform and arranged for engagement with frontal areas of selected portions of the infant's body to restrain such body portions against being raised out of said depression, the sides of said depression in the various portions of such depression extending materially upward along the respectively adjacent sides of the corresponding portions of the infant's body and thereby limiting lateral movement of the infant.

*5. The infant immobilizing device for surgical use and the like, comprising a generally horizontally disposable infant supporting platform of substantially rigid solid sheet form having a depression therein conformed approximately to the dorsal side of a small infant's body, said depression including conjoining portions formed to provide underlying and close lateral support for at least the torso and legs of the infant placed in dorsal recumbent position therein, said platform having a generally horizontally disposed marginal portion substantially surrounding the peripheral edge of the depression, said leg portions being divergent to provide space therebetween, and an instrument table portion located directly between the two leg portions of said depression, and releasable holder means adapted for connection to said platform and arranged for engagement with frontal areas of selected portions of the infant's body to restrain such body portions against being raised out of said depression, the sides of said depression extending materially upward along the respectively adjacent sides of the infant's body and thereby limiting lateral movement of the infant.*

*6. The infant immobilizing device for surgical use and the like, comprising a generally horizontally disposable infant supporting platform of substantially rigid solid sheet form having a depression therein conformed approximately to the dorsal side of a small infant's body, said depression including conjoining portions formed to provide underlying and close lateral support for at least the torso and legs of the infant placed in dorsal recumbent position therein, said platform having a generally horizontally disposed marginal portion substantially surrounding the peripheral edge of the depression, said leg portions being divergent to provide space therebetween, and releasable holder means adapted for connection to said platform and arranged for engagement with frontal areas of selected portions of the infant's body to restrain such body portions against being raised out of said depression, the sides of said depression extending materially upward along the respectively adjacent sides of the infant's body and thereby limiting lateral movement of the infant.*

References Cited in the file of this patent or the original patent

UNITED STATES PATENTS

| | | |
|---|---|---|
| 322,437 | Gaston | July 21, 1885 |
| 1,980,848 | Cass | Nov. 13, 1934 |
| 2,376,507 | Ruther | May 22, 1945 |
| 2,454,802 | Hipps | Nov. 30, 1948 |
| 2,459,729 | Treace | Jan. 18, 1949 |
| 2,465,781 | Banta | Mar. 29, 1949 |
| 2,671,442 | Cameto | Mar. 9, 1954 |
| 2,700,381 | Powell | Jan. 25, 1955 |

FOREIGN PATENTS

| | | |
|---|---|---|
| 268 | Great Britain | 1892 |